United States Patent [19]

Arndt

[11] Patent Number: 5,616,779

[45] Date of Patent: Apr. 1, 1997

[54] PROCESS FOR THE PREPARATION OF 2,5-DI-PHENYLAMINO-TEREPHTHALIC ACID AND ITS DIALKYL ESTERS

[75] Inventor: Otto Arndt, Hofheim/Ts, Germany

[73] Assignee: Hoechst AG, Germany

[21] Appl. No.: 397,733

[22] Filed: Mar. 2, 1995

Related U.S. Application Data

[63] Continuation of Ser. No. 59,816, May 10, 1993, abandoned.

[30] Foreign Application Priority Data

May 12, 1992 [DE] Germany .................. 42 15 685.8

[51] Int. Cl.⁶ .................. C07C 101/38; C07C 101/68; C07C 103/76
[52] U.S. Cl. .................. 560/48; 562/457; 546/49
[58] Field of Search .................. 562/457; 560/48; 546/49

[56] References Cited

U.S. PATENT DOCUMENTS

| | | | |
|---|---|---|---|
| 3,342,823 | 9/1967 | Dien | 260/279 |
| 3,555,087 | 1/1971 | Grosso et al. | 260/558 |
| 3,671,451 | 6/1972 | Butterfield | 252/301.2 |
| 4,435,589 | 3/1984 | Rolf et al. | 560/48 |
| 4,981,997 | 1/1991 | Schmirtz et al. | 562/457 |
| 5,208,365 | 5/1993 | Ohno et al. | 562/457 |

FOREIGN PATENT DOCUMENTS 0373959  6/1990  European Pat. Off. .

OTHER PUBLICATIONS

Chemical Abstracts, vol. 102, Abstract No. 5780p, "Rhodium (II) acetate catalyzed hydrocarbon oxidations by molecular oxygen", p. 525, 1990.

Primary Examiner—Marianne M. Cintins
Assistant Examiner—Keith MacMillan
Attorney, Agent, or Firm—Connolly & Hutz

[57] ABSTRACT

The present invention relates to a process for the preparation of 2,5-di-phenylamino-terephthalic acid and its dialkyl esters of the formula

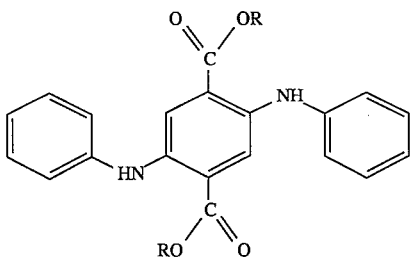

in which R is a hydrogen atom or a methyl or an ethyl group, by reaction of a succinic acid dialkyl ester with a sodium alcoholate in xylene, treatment of the resulting 2,5-dihydroxy-cyclohexadiene-1,4-di-carboxylic acid dialkyl ester with acid and aniline, dehydrogenation of the resulting 2,5-di-phenylamino-dihydro-(3,6)-terephthalic acid dialkyl ester by means of oxygen, if appropriate hydrolysis of the 2,5-di-phenylamino-terephthalic acid dialkyl ester formed and liberation of the 2,5-di-phenylamino-terephthalic acid from the di-sodium salt formed. The 2,5-di-phenylamino-dihydro-(3,6)-terephthalic acid dialkyl ester is reacted with pure oxygen in the presence of an alkali metal ion and/or an alkaline earth metal ion. This significantly decreases undesirable impurities.

21 Claims, No Drawings

PROCESS FOR THE PREPARATION OF 2,5-DI-PHENYLAMINO-TEREPHTHALIC ACID AND ITS DIALKYL ESTERS

This application is a continuation of Ser. No. 08/059,816, filed May 10, 1993, now abandoned.

The present invention relates to a process, which is improved in the economic respect and in matters of environmental protection, for the preparation of 2,5-di-phenylamino-terephthalic acid and its dialkyl esters, in particular its methyl and ethyl esters.

It is known that 2,5-di-phenylamino-terephthalic acid and dialkyl esters thereof can be prepared via a multi-stage process, in which, in a first step, a succinic acid dialkyl ester is cyclized by a Dieckmann or double Claisen condensation to give the corresponding 2,5-di-hydroxy-cyclohexadiene-1,4-dicarboxylic acid dialkyl ester, this is then converted by condensation with a primary phenylamine (for example aniline or toluidine) in xylene or ethylbenzene or mixtures thereof in the presence of an aliphatic acid (for example acetic acid) into the corresponding 2,5-di-phenylaminD-dihydro-(3,6)-terephthalic acid dialkyl ester, this is converted by oxidation (dehydrogenation) into the corresponding 2,5-di-phenylamino-terephthalic acid dialkyl ester, this ester is then hydrolyzed by means of alcoholic sodium hydroxide solution, and the free 2,5-di-phenylamino-terephthalic acid is liberated from the resulting sodium salt of 2,5-di-phenylamino-terephthalic acid by means of an acid.

This type of preparation is described in DE-A-1 915 436 and DE-A-3 834 747 (EP 0 363 756), a number of process parameters being described, such as the nature of the solvent, isolation of individual products or of all the products obtained in the multi-stage synthesis (these include the 2,5-dihydroxy-cyclohexadiene-1,4-dicarboxylic acid dialkyl ester, 2,5-di-phenylamino-dihydro-(3,6)-terephthalic acid di-alkyl ester, 2,5-di-phenylamino-terephthalic acid di-alkyl ester and 2,5-di-phenylamino-terephthalic acid), and furthermore the nature of the catalysts used, if appropriate with additives for the individual synthesis steps, the sequence of oxidation and hydrolysis with respect to time (simultaneous oxidation and hydrolysis or successive), oxidizing agents, such as nitrobenzene and derivatives thereof, quinones, oxygen or iodine, and working up of the auxiliaries used, such as solvents, phenylamine (secondary product of nitrobenzene), catalysts and other additives.

For reasons of environmental protection, it is not particularly appropriate to use the nitroaromatics (nitrobenzene or derivatives, such as nitrobenzene-m-sulfonic acid) recommended as oxidizing agents for the dehydrogenation stage, instead of air or oxygen. A substance such as nitrobenzene should at the most be used as a unit in syntheses, but not as auxiliary, since its second products, such as aniline and azo- or azoxybenzene, have to be removed at great expense and cannot be reutilized because of the unavoidable large amounts of impurities which arise. They are thus produced as waste substances which pollute the environment and either pollute the waste water or must be dumped.

Processes which use air in association with additives (quinones and derivatives thereof, such as sulfonic acid and chloranil, or quaternary ammonium salts) as the oxidizing agent in the oxidation stage (EP-57 873 and EP-363 576) are likewise to be evaluated as unfavorable for reasons of environmental protection, since these additives in general enter into the waste water and in some cases are a severe hazard to water. Recovery of the additives is not envisaged in any of the abovementioned processes.

The process according to DE-OS-1 915 436 has a number of disadvantages. On the one hand, the 2,5-di-phenylamino-terephthalic acid dialkyl ester crude product formed in the oxidation stage is obtained, after filtration, as a xylene-containing mixture from which the xylene must be removed by washing, for example with acetone. This mixture of acetone and xylene must be worked up separately. On the other hand, additional recrystallization of the crude product is evidently still necessary, in order to arrive at a sufficiently pure product. Because of the solubility of the ester in xylene, the mixture must be cooled to a temperature of less than 15° C. before the filtration, which requires a not inconsiderable industrial expenditure. Moreover, the majority of the by-products are found in the xylene filtered off. This means that on recovery of the xylene by distillation, a tarry bottom product is obtained, which can be disposed of only by combustion. Finally, an impurity which separates out as a thin, dark brown deposit of a solid on the wall of the reaction vessel and on the stirrer forms in the course of the oxidation.

Summarizing, it can be said both that isolation of the 2,5-di-phenylamino-terephthalic acid dialkyl ester is associated with considerable industrial expenditure, and that disadvantages in ecology matters also have to be accepted in respect of disposal of the waste products.

On the basis of the above comments, there is a need for a process which avoids the disadvantages described above and moreover can be carried out easily and with the aid of readily accessible auxiliaries.

This object is achieved by a process for the preparation of 2,5-di-phenylamino-terephthalic acid and its dialkyl esters of the formula

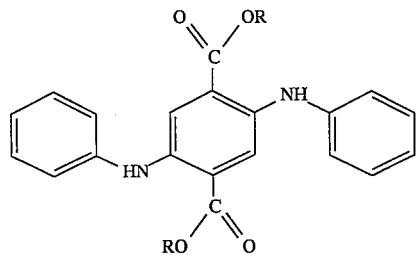

in which R is a hydrogen atom or a methyl or an ethyl group, by reaction of a succinic acid dialkyl ester with a sodium alcoholate in xylene, treatment of the resulting 2,5-dihydroxy-cyclohexadiene-1,4-di-carboxylic acid dialkyl ester with acid and aniline, dehydrogenation of the resulting 2,5-di-phenylamino-dihydro-(3,6)-terephthalic acid dialkyl ester by means of oxygen, if appropriate hydrolysis of the resulting 2,5-di-phenylamino-terephthalic acid dialkyl ester with methanolic sodium hydroxide solution and liberation of 2,5-di-phenylamino-terephthalic acid from the 2,5-di-phenylamino-terephthalic acid di-sodium salt formed, which comprises reacting the 2,5-di-phenylamino-dihydro-(3,6)-terephthalic acid dialkyl ester with pure oxygen in the presence of an alkali metal ion and/or alkaline earth metal ion.

One advantage of the process is that the use of oxygen leads to only one reaction product, that is to say water. Furthermore, it is possible to use a single solvent in all the individual steps of the multi-stage synthesis. Xylene, for example, has proven to be suitable.

Another important advantage of the process is that the dark brown deposit which separates out on the wall and on the stirrer in the reaction vessel also no longer occurs.

The process according to the invention has a favorable effect on the quality of the free 2,5-di-phenylamino-terephthalic acid. The free 2,5-di-phenylamino-terephthalic acid prepared by the process of the prior art usually still contains impurities within a certain range, these making up between about 0.5 to 1.0%, based on the total product, as demonstrated by HPLC (high performance liquid chromatography) and HPTLC (high performance thin layer chromatography) studies. This impurity, in particular one of its components, is surprisingly decreased considerably by the process according to the invention.

The amount of alkali metal ions or alkaline earth metal ions required for carrying out the process according to the invention successfully is comparatively low and corresponds to catalytic amounts. In general, it is sufficient to employ 0.2 to 12.0, in particular 0.8 to 6.0 mol % of alkali metal ions or alkaline earth metal ions, based on the 2,5-di-phenylamino-dihydro-(3,6)-terephthalic acid dialkyl ester.

Because of the small amount and the nature of the additives used (alkali metal ions or alkaline earth metal ions), pollution of the waste water can be kept low and the process can be carried out in an environment-friendly manner.

The by-products are advantageously distributed between the aqueous mother liquor and the methanolic wash filtrate such that the content in the waste water is biodegradable to the extent of more than 98% (measured as eliminability according to DIN 38412-L25), and the content in the methanol is only about 33 to about 50% of the amount obtained by the process of DOS 195436, and therefore significantly less organic product must be disposed of by combustion.

It has proved to be advantageous to use $Na^+$ or $K^+$ as the alkali metal ion and $Mg^{2+}$, $Ca^{2+}$ or $Sr^{2+}$ as the alkaline earth metal ion.

The process can be carried out in a particularly simple manner by employing the alkali metal ions or alkaline earth metal ions in the form of alkali metal oxides or alkaline earth metal oxides, alkali metal salts or alkaline earth metal salts, in particular carbonates or carboxylic acid salts. It has proved particularly appropriate to use alkali metal salts or alkaline earth metal salts of aliphatic carboxylic acids, in particular of aliphatic monocarboxylic acids having 2 to 8 carbon atoms. It is particularly easy to use alkali metal acetates or alkaline earth metal acetates.

It has proved to be particularly appropriate to carry out the oxidation in a closed system, i.e. under the particular autogenous pressure established. Nevertheless, it is also possible to allow the oxidation to proceed in an open system.

The oxidation is usually carried out at 95 to 110, in particular 98° to 103° C. The oxidation can be carried out either under atmospheric pressure or under increased pressure. Suitable pressures are 0.1 to 1.0, in particular 0.1 to 0.5 MPa. However, the oxidation can also be carried out under pressures above 1.0 MPa, a correspondingly higher industrial expenditure being required. o-Xylene, m-xylene or ethylbenzene, in particular industrial xylene, have proven to be suitable solvents. Industrial xylene is the commercially available mixture of isomeric xylenes, which additionally comprises ethylbenzene.

According to a preferred process variant, the oxidation is first carried out using xylene as the solvent, the xylene is then removed by steam distillation after the oxidation has been concluded, the 2,5-di-phenylamino-terephthalic acid dialkyl ester formed is filtered off, the ester which has been filtered off is washed with an aliphatic alcohol, in particular methanol, ethanol or propanol, preferably methanol, and the 2,5-di-phenylamino-terephthalic acid dialkyl ester which has been purified by the washing operation is then dried.

As can be seen from DE-OS-1 915 436, 2,5-di-phenylamino-terephthalic acid and its esters are important starting substances for the preparation of luminescent compositions.

The 2,5-di-phenylamino-terephthalic acid prepared according to the invention and its esters are particularly suitable for the preparation of quinacridones.

The following examples document the invention, without limiting it.

EXPERIMENTAL PART

EXAMPLE 1

Preparation of Dimethyl 2,5-di-phenylamino-cyclohexadiene 1,4-dicarboxylate 500 parts of xylene of industrial quality (commercially available isomer mixture which additionally comprises ethylbenzene) and 85 parts of propionic acid (about 99% pure) are initially introduced into a glass apparatus fitted with a stirrer, a reflux condenser, a water separator for removing water from the circulation and a connection for passing in nitrogen. 114 parts of dimethyl 2,5-di-hydroxy-cyclohexadiene-1,4-dicarboxylate (about 97 to 98% pure) are introduced under nitrogen protection. 112 parts of aniline are then added at about 75°–90° C., while still under nitrogen and while stirring. The mixture of starting substances is heated up from 90° to about 98° to 100° C. in the course of about 3 hours, while passing nitrogen through, and is allowed to after-react for a further 45 minutes, while continuing to pass nitrogen through, in order to bring the reaction to completion (quantitative separation of the theoretical amount of water of reaction).

Preparation of Methyl 2,5-di-phenylamino-terephthalate 1.3 parts of magnesium acetate tetrahydrate are added to the mixture containing dimethyl 2,5-di-phenylamino-cyclohexadiene-1,4-dicarboxylate. Instead of nitrogen, a stream of pure oxygen (3 liters/hour) is now passed in via a cylindrically widened feed tube, which is connected to a gauze of high-grade steel for better distribution of the stream of oxygen. The mixture is heated up to a temperature of about 98° to 100° C. The cyclohexadiene ring is oxidized to a benzene ring by the oxidation (dehydro-genation) which now starts. Water of reaction is again formed here, and is entrained by a stream of nitrogen (12 liters/hour) passed over the starting mixture and is subsequently removed from the reaction system via the water separator after condensation in the reflux condenser. The oxidation has ended after about 2.5 hours, as can be seen by the end of the removal of water. The reaction is additionally checked by liquid chromatography (HPLC).

Dimethyl 2,5-di-phenylamino-terephthalate is Obtained in the Form of a Dark-colored Solution The xylene employed as the solvent is then removed by passing in steam (steam distillation), the dimethyl 2,5-di-phenylamino-terephthalate precipitating as a solid. It is filtered off with the aid of a suction filter at 80° C. and washed with boiling hot water, and steam is blown through the dimethyl ester crude product on the suction filter for about 15 minutes. This product is then washed with about 500–700 parts of methanol at 50° C. to give, after drying in a drying oven, 173.1 parts of dimethyl 2,5-di-phenylamino-terephthalate (corresponding to a yield of 92.0%, based on the dimethyl 2,5-di-hydroxy-cyclohexadiene-1,4-dicarboxylate employed) with a melting point of about 160°–163° C.

The methanol used for the washing is worked up by distillation, and a tarry residue containing 14.1 parts of solid, which is disposed of by combustion, is obtained.

The entire waste water obtained on steam distillation of the xylene and the filtration of the crude dimethyl ester has an organic carbon content of about 50 parts and has a COD elimination of more than 98%.

Preparation of 2,5-di-phenylamino-terephthalic Acid

The dimethyl 2,5-di-phenylamino-terephthalate is employed directly immediately after being washed with methanol, drying being dispensed with, and is hydrolyzed with a mixture of methanol, water and sodium hydroxide solution in a stirred autoclave at 106° C. in the course of 3 hours to give the corresponding di-sodium salt. The alkaline solution of the reaction mixture is filtered under nitrogen protection and then freed from the methanol by distillation. 2,5-Di-phenylamino-terephthalic acid is precipitated out of the virtually methanol-free solution with concentrated hydrochloric acid.

154.7 parts of 2,5-di-phenylamino-terephthalic acid (corresponding to a yield of 88.8%, based on the dimethyl 2,5-di-hydroxy-cyclohexadiene-1,4-dicarboxylate) with a melting point of 319° C. (decomposition) are obtained.

The reverse phase HPLC chromatogram shows, in the retention range below the 2,5-di-phenylamino-terephthalic acid, a peak of a component with a retention time of 5.0 minutes, corresponding to an intensity of 0.196 percent by area.

EXAMPLE 2

The procedure is as described in Example 1, but instead of magnesium acetate tetrahydrate, 0.337 part of calcium acetate (94% pure) is added.

172.4 parts of dimethyl 2,5-di-phenylamino-terephthalate (corresponding to a yield of 91.6%, based on the dimethyl 2,5-di-hydroxy-cyclohexadiene-1,4-dicarboxylate employed) with a melting point of about 159° to 162° C. are obtained.

After the methanol obtained during washing of the dimethyl ester has been worked up by distillation, a tarry residue containing 15.9 parts of solid is obtained.

Hydrolysis and acidification gives 153.0 parts of 2,5-di-phenylamino-terephthalic acid (corresponding to a yield of 87.9%, based on the dimethyl 2,5-di-hydroxy-cyclohexadiene-1,4-dicarboxylate) with a melting point of 318° C. (decomposition).

The reverse phase HPLC chromatogram shows, in the retention range below the 2,5-di-phenylamino-terephthalic acid, the peak of the component corresponding to an intensity of 0.135 percent by area.

EXAMPLE 3

The procedure is as described in Example 1, but instead of magnesium acetate tetrahydrate, 0.595 part of potassium acetate (99% pure) is added. 173.1 parts of dimethyl 2,5-di-phenylamino-terephthalate (corresponding to a yield of 92.0%, based on the dimethyl 2,5-di-hydroxy-cyclohexadiene-1,4-dicarboxylate employed) with a melting point of about 158° to 162° C. are obtained.

After the methanol obtained during washing of the dimethyl ester has been worked up by distillation, a tarry residue containing about 16.5 parts of solid is obtained.

Hydrolysis and acidification gives 156.6 parts of 2,5-di-phenylamino-terephthalic acid (corresponding to a yield of 89.9%, based on the dimethyl 2,5-di-hydroxy-cyclohexadiene-1,4-dicarboxylate) with a melting point of 316° C. (decomposition).

The reverse phase HPLC chromatogram shows, in the retention range below the 2,5-di-phenylamino-terephthalic acid, the peak of the component with the retention time of 5.0 minutes, corresponding to an intensity of 0.176 percent by area.

EXAMPLE 4

The procedure is as described in Example 1, but instead of magnesium acetate, 5.0 parts of sodium acetate (99% pure) (=12 mol %) are added. 173.2 parts of dimethyl 2,5-di-phenylamino-terephthalate (corresponding to a yield of 90.2%, based on the dimethyl 2,5-di-hydroxy-cyclohexadiene-1,4-dicarboxylate employed) with a melting point of about 158°–162° C. are obtained.

After the methanol obtained during washing of the dimethyl ester has been worked up by distillation, a tarry residue containing 16.8 parts of solid is obtained.

Hydrolysis and acidification gives 156.0 parts of 2,5-di-phenylamino-terephthalic acid (corresponding to a yield of 89.6%, based on the dimethyl 2,5-di-hydroxy-cyclohexadiene-1,4-dicarboxylate) with a melting point of 318° C. (decomposition).

The reverse phase HPLC chromatogram shows, in the retention range below the 2,5-di-phenylamino-terephthalic acid, the peak of the component corresponding to an intensity of 0.122 percent by area.

Comparison Example 1

The procedure is as described in Example 1, but without addition of magnesium acetate tetrahydrate. 176.0 parts of dimethyl 2,5-di-phenylamino-terephthalate (corresponding to a yield of 93.5%, based on the dimethyl 2,5-di-hydroxy-cyclohexadiene-1,4-dicarboxylate employed) with a melting point of about 159° to 161° C. are obtained. In the oxidation stage, a thin, dark brown deposit of a solid forms on the wall of the glass apparatus and on the stirrer.

After the methanol obtained during washing of the crude dimethyl ester has been worked up by distillation, a tarry residue containing 11.8 parts of solid is obtained. Hydrolysis and acidification gives 158.0 parts of 2,5-di-phenylamino-terephthalic acid (corresponding to a yield of 90.7%, based on the dimethyl 2,5-di-hydroxy-cyclohexa-diene-1,4-dicarboxylate) with a melting point of about 316° C. (decomposition).

The reverse phase HPLC chromatogram shows the peak of the component with a retention time of 5 minutes, corresponding to an intensity of 0.527 percent by area.

I claim:

1. A process for the preparation of 2,5-di-phenylamino-terephthalic acid or one of its dialkyl esters of the formula

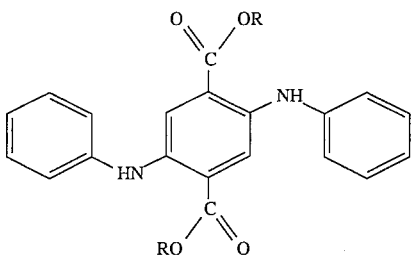

in which R is a hydrogen atom or a methyl or an ethyl group, comprising reacting a 2,5-dihydroxycyclohexadiene-1,6-dicarboxylic acid dialkyl ester with aniline in a solvent in the presence of acid; and by dehydrating the resulting 2,5-di-phenylamino-dihydro-(3.6)-terephthalic acid dialkyl ester by means of pure oxygen in the presence of acid and in the presence of an alkali metal ion and/or alkaline earth metal ion, at a temperature of 95° to 110° C.; and optionally hydrolyzing the resulting 2,5-di-phenylamino-terephthalic acid dialkyl ester.

2. The process as claimed in claim 1, wherein $Na^+$ or $K^+$ is employed as the alkali metal ion and $Mg^{2+}$, $Ca^{2+}$ or $Sr^{2+}$ is employed as the alkaline earth metal ion.

3. The process as claimed in claim 1, wherein an alkali metal salt or alkaline earth metal salt of an aliphatic carboxylic acid is the alkali metal salt or alkaline earth metal salt which is present in the reaction zone.

4. The process as claimed in claim 3, wherein an alkali metal acetate or alkaline earth metal acetate is the alkali metal salt or alkaline earth metal salt which is present in the reaction zone.

5. The process as claimed in claim 4, further comprising a step of hydrolysis of the resulting 2,5-di-phenylamino-terephthalic acid dialkyl ester with methanolic sodium hydroxide solution is performed after the oxidation step and said reaction is carried out in said reaction zone which is a dosed system at a temperature of 98° to 103° C., under a pressure of 0.1 to 0.5 MPa.

6. The process as claimed in claim 5, wherein xylene is present in said reaction zone and xylene is removed by steam distillation after the reaction in said reaction zone has been completed, and the 2,5-di-phenylamino-terephthalic acid dialkyl ester thus obtained is filtered off, washed of methanol, ethanol or propanol, and dried.

7. The process as claimed in claim 1, wherein said reaction zone is a closed system.

8. The process as claimed in claim 1, wherein the reaction carried out in said reaction zone is carried out under a pressure of 0.1 to 1.0 MPa.

9. The process as claimed in claim 1, wherein a solvent is present in said reaction zone, said solvent being xylene.

10. The process as claimed in claim 1, wherein a solvent is present in said reaction zone, and this solvent is removed by steam distillation after the reaction in said reaction zone has been concluded, and the 2,5-di-phenylaminoterephthalic acid dialkyl ester thus obtained is filtered off, washed with an aliphatic alcohol and dried.

11. The process as claimed in claim 10, wherein the solvent comprises xylene.

12. The process as claimed in claim 1, wherein the reaction in the reaction zone is carried out in the presence of 0.8 to 6.0 mol % of alkali metal ion or alkaline earth metal ion, based on the 2,5-di-phenylamino-dihydro-(3,6)-terephthalic acid dialkyl ester.

13. The process as claimed in claim 1, wherein the alkali metal salt or alkaline earth metal salt is a carbonate or a carboxylic acid salt.

14. The process as claimed in claim 13, wherein the carboxylic acid salt is a salt of an aliphatic monocarboxylic acid having 2 to 8 carbon atoms.

15. The process as claimed in claim 14, wherein the reaction in the reaction zone is carried out at 98° to 103° C., under a pressure of 0.1 to 0.5 MPa.

16. A process for the preparation of a quinacridone, comprising:

preparing 2,5-di-phenylamino-terephalic acid or an ester thereof according the process as claimed in claim 1, and converting the resulting 2,5-diphenylamino-terephthalic acid or ester thereof into the quinacridone.

17. The process as claimed in claim 1, further comprising a step of hydrolysis of the resulting 2,5-di-phenylamino-terephthalic acid dialkyl ester with methanolic sodium hydroxide solution is performed after the oxidation step.

18. The process as claimed in claim 1, wherein the process consists of reacting the 2,5-di-phenylamino-dihydro-(3,6-terephthalic acid dialkyl ester with pure oxygen in the reaction zone in the presence of 0.2 to 12 mol % of an alkali metal ion and/or alkaline earth metal ion based on the 2,5-di-phenylamino-dihydro-(3,6)-terephthalic acid dialkyl ester wherein an alkali metal oxide or alkaline earth metal oxide, alkali metal salt or alkaline earth metal salt is present in said reaction zone to provide the alkali metal ion or alkaline earth metal ion or combination of alkali metal and alkaline earth metal ions and wherein the reaction is carried out in said reaction zone at a temperature from 98° to 103° C.

19. The process as claimed in claim 1, wherein said solvent is xylene and said alkali metal ion and/or alkaline earth metal ion is present in an amount from 0.2 to 12 mol % of the based on the 2,5-di-phenylamino-dihydro-(3,6)-terephthalic acid dialkyl ester.

20. A process for the preparation of 2,5-di-phenylamino-terephtalic acid or a dialkyl ester thereof, comprising the step or steps of:

reacting a dialkyl ester of 2,5-di-phenylamino-dihydro-(3,6)-terephthalic acid with pure oxygen, in a reaction zone, in the presence of an alkali metal ion or an alkaline earth metal ion or a combination of alkali metal and alkaline earth metal ions, and optionally hydrolyzing the resulting 2,5-di-phenylamino-terephthalic acid dialkyl ester to obtain the 2,5-di-phenylamino-terephthalic acid.

21. The process as claimed in claim 20, wherein the resulting 2,5-di-phenylamino-terephthalic acid dialkyl ester is treated with methanolic sodium hydroxide, and the 2,5-di-phenylamino-terephthalic acid is liberated from the thus-formed di-sodium salt.

* * * * *